(12) United States Patent
Nakanishi et al.

(10) Patent No.: US 7,070,411 B2
(45) Date of Patent: Jul. 4, 2006

(54) DENTAL HEAD UNIT CAPABLE OF MEASURING ROOT CANAL LENGTH, AND CONTACT HOLDER ASSEMBLY THEREFOR

(75) Inventors: Eiichi Nakanishi, Kanuma (JP); Masanori Mizunuma, Utsunomiya (JP)

(73) Assignee: Nakanishi Inc., Kanuma (JP)

( * ) Notice: Subject to any disclaimer, the term of this patent is extended or adjusted under 35 U.S.C. 154(b) by 289 days.

(21) Appl. No.: 10/659,274

(22) Filed: Sep. 11, 2003

(65) Prior Publication Data
US 2004/0152040 A1 Aug. 5, 2004

(30) Foreign Application Priority Data
Feb. 5, 2003 (JP) .............................. 2003-027811

(51) Int. Cl.
*A61C 19/04* (2006.01)

(52) U.S. Cl. .............................. 433/72; 433/27; 433/75

(58) Field of Classification Search .................. 433/27, 433/72, 75, 77, 98, 102, 123, 80–81, 129
See application file for complete search history.

(56) References Cited
U.S. PATENT DOCUMENTS

| 5,897,315 A | * | 4/1999 | Nakayama et al. ........... 433/72 |
| 5,902,105 A | | 5/1999 | Uejima et al. |
| 6,520,773 B1 | | 2/2003 | Weber |
| 6,845,265 B1 | * | 1/2005 | Thacker ...................... 600/547 |

* cited by examiner

*Primary Examiner*—Cary E. O'Connor
*Assistant Examiner*—Patrick J. Kilkenny
(74) *Attorney, Agent, or Firm*—Novak Druce & Quigg, LLP; Jason D. Voight

(57) ABSTRACT

The present invention relates to a dental head unit capable of measuring a root canal length of a patient. The head unit includes a head section having a sleeve rotatably supported therein for detachably holding a cutting tool therein, a neck section extending proximally from the head section and having a proximal end for connecting to a handpiece body, a contact capable of detachably contacting the cutting tool for providing electric connection to the cutting tool when in contact, and a contact holder fixed to a proximal end of the contact and axially slidable with respect to the neck section. The contact holder has a lead attachment to which a lead for electrically connecting the contact to a root canal length measuring device is detachably attached. The present invention also relates to a contact holder assembly including the contact and the contact holder.

5 Claims, 4 Drawing Sheets

DENTAL HEAD UNIT CAPABLE OF MEASURING ROOT CANAL LENGTH, AND CONTACT HOLDER ASSEMBLY THEREFOR

FIELD OF ART

The present invention relates to a dental head unit for root canal therapy and measurement of the root canal length, and a contact holder assembly for use with such a dental head unit.

BACKGROUND ART

Pulpectomy has widely been performed for treatment of pulpitis, which includes removal of the dental pulp, enlargement and cleaning of the root canal. Various devices have been proposed for performing such a treatment, including hand reamers, engine reamers, and engine files.

An example of an endodontic handpiece for electrically driving a cutting tool, such as a reamer or a file, used for root canal therapy is schematically shown in FIG. 4. The endodontic handpiece includes handpiece body 1A generally in an elongated cylindrical form, and head unit 1B detachably threaded onto the handpiece body 1A. The handpiece body 1A accommodates therein a motor driven by, for example, an external power supply or a rechargeable battery. This motor is operated by pressing power switch 4 provided projecting on the handpiece body 1A in its distal portion. The head unit 1B includes neck section 2 and head section 3 integrally connected to the distal end of the neck section 2. Cutting tool 5 is detachably mounted on the head section 3 and driven by the motor for endodonic treatment.

During treatment with such an electrically driven handpiece, it is demanded that the same handpiece is also capable of precisely measuring the length of the root canal. For this purpose, there have been proposed handpieces that employ the cutting tool as a probe to enable measurement of the length of the root canal during the root canal therapy.

For example, JP-9-224961-A discloses a handpiece having a root canal length measurement function, which enables measurement of the root canal length while giving the root canal therapy. This handpiece has incorporated inside a signal circuit for sending measurement signals from a root canal length measurement circuit to a measurement probe mounted on a head provided at the tip of the handpiece, and the signal circuit is electrically connected to the measurement probe via a contact piece. The contact piece is provided on the lower surface of the head and supported so as to be rotatable vertically in the axial direction of the measurement probe. The contact piece holds the measurement probe between the tip portions thereof when rotated in the upward direction that makes contact with the measurement probe.

In this handpiece, the contact piece is made vertically rotatable on the lower surface of the head by pivotally connecting the contact piece to a separately provided contact plate, which requires bothersome production and assembly of these parts. Further, possibility of improper contact between the contact piece and the contact plate in the pivoting region cannot be eliminated.

SUMMARY OF THE INVENTION

It is therefore an object of the present invention to provide a dental head unit for root canal therapy and measurement of the root canal length, which ensures proper electrical contact between the parts, and of which parts are produced and assembled relatively easily.

It is another object of the present invention to provide a contact holder assembly for use with the above dental head unit, which ensures proper electrical contact between the parts, and which are easily to produce and assemble.

According to the present invention, there is provided a dental head unit capable of measuring a root canal length of a patient, comprising:
 a head section having a sleeve rotatably supported therein for detachably holding a cutting tool therein;
 a neck section extending proximally from said head section and having a proximal end for connecting to a handpiece body;
 a contact capable of detachably contacting the cutting tool for providing electric connection to the cutting tool when in contact; and
 a contact holder fixed to a proximal end of said contact and axially slidable with respect to said neck section, said contact holder has a lead attachment to which a lead for electrically connecting said contact to a root canal length measuring device is detachably attached.

According to the present invention, there is also provided a contact holder assembly for use with the above-mentioned dental head unit having a head section and a neck section, comprising:
 a contact capable of detachably contacting a cutting tool held in a head section of a dental head unit for providing electric connection to the cutting tool when in contact; and
 a contact holder fixed to a proximal end of said contact and axially slidable with respect to a neck section of the dental head unit, said contact holder has a lead attachment to which a lead for electrically connecting said contact to a root canal length measuring device is detachably attached.

In the dental head unit of the present invention, the contact is fixed to the contact holder, and is brought into or out of contact with the cutting tool simply by sliding the contact holder with respect to the neck section. Thus the risk of improper electrical connection to occur in the internal wiring from the contact to the root canal length measuring device is remarkably reduced.

Further, electrical connection between the contact and the root canal length measuring device is established simply by detachably connecting a lead from the root canal length measuring device to the lead attachment provided in the contact holder. Thus a root canal length measuring circuit is not necessarily provided in the handpiece body, and production and assembly of the dental head unit per se is simplified.

BRIEF DESCRIPTION OF THE DRAWINGS

By way of example, preferred embodiments of the present invention will now be described with reference to the accompanying drawings, in which.

PREFERRED EMBODIMENTS OF THE INVENTION

Figure 1:
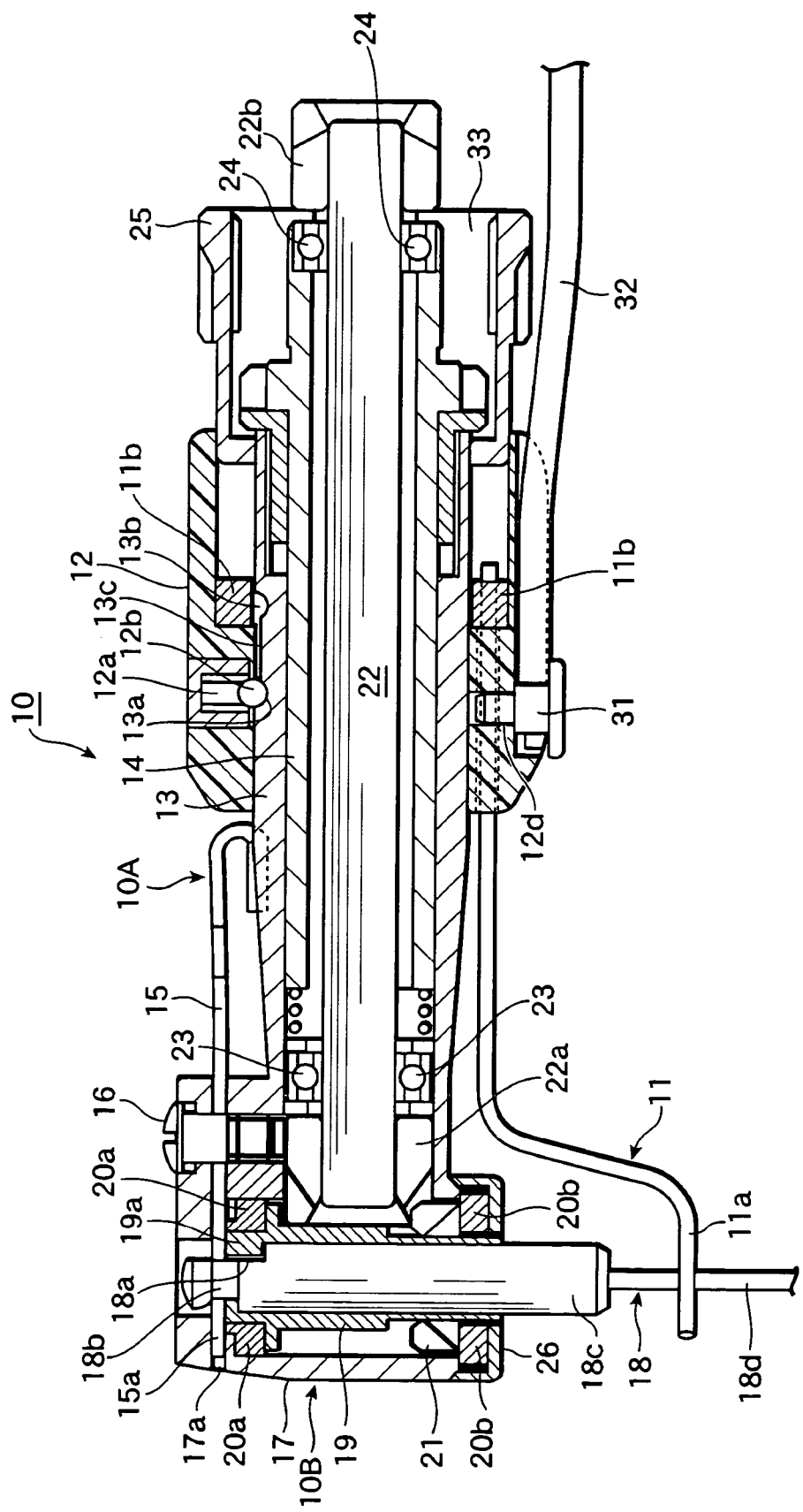
FIG. 1 is a longitudinal sectional view, partially elevational, of an embodiment of the dental head unit according to the present invention.
Figure 2:
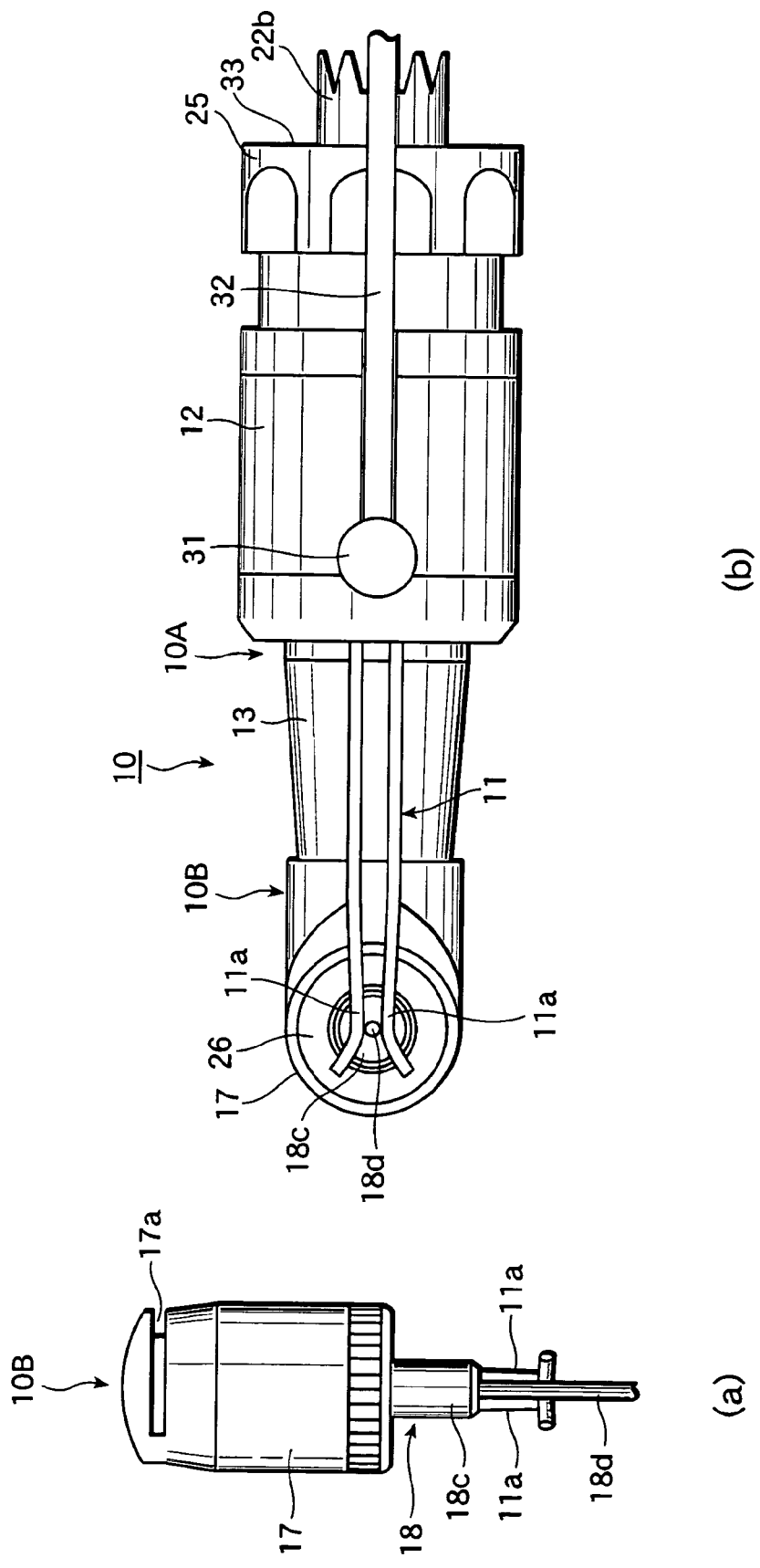
FIG. 2(a) is a front view of the dental head unit of FIG. 1.
FIG. 2(b) is a bottom view thereof.
Figure 3:
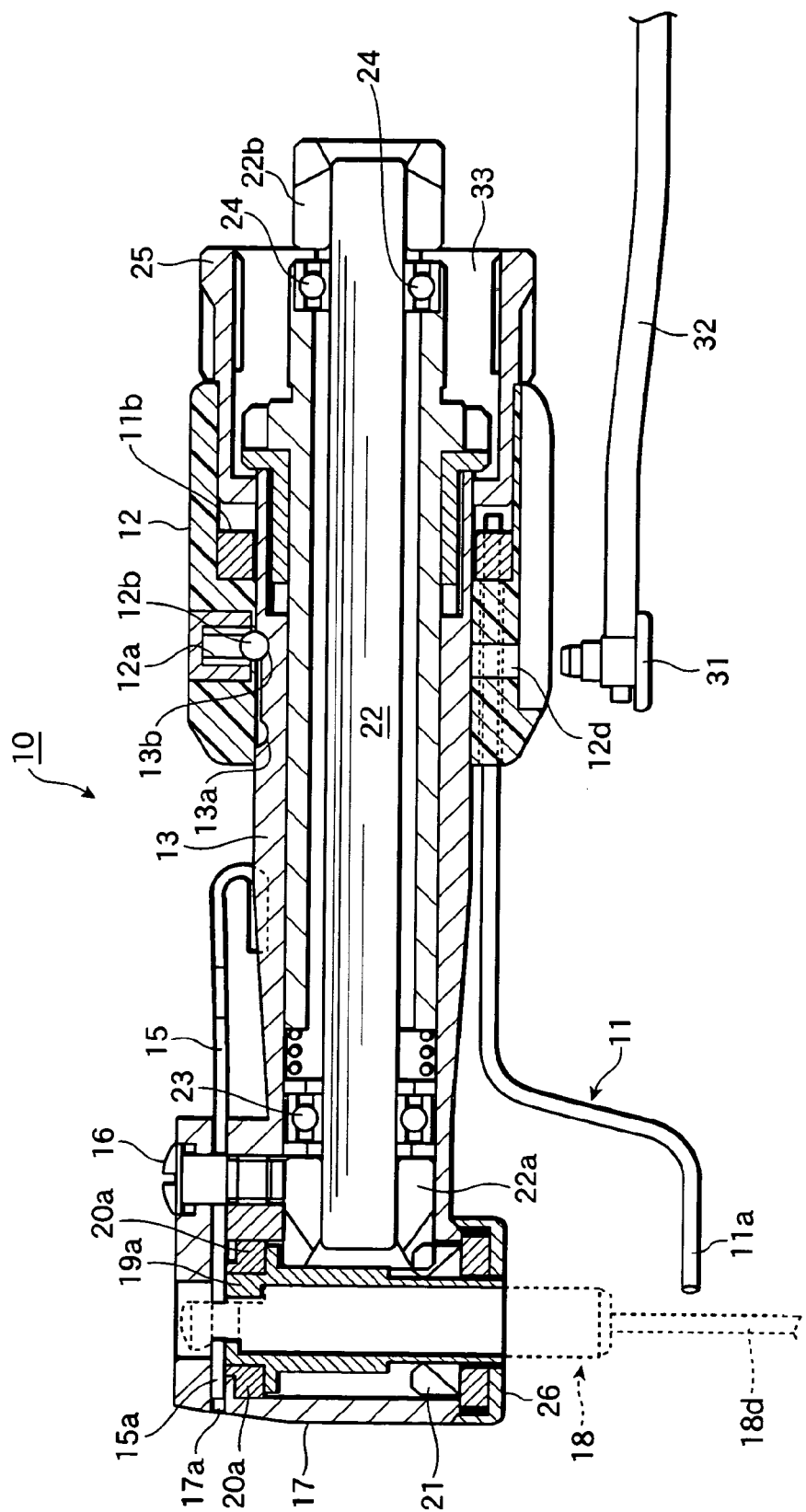
FIG. 3 is a longitudinal sectional view similar to FIG. 1, with some parts being removed for the sake of explanation.
Figure 4:
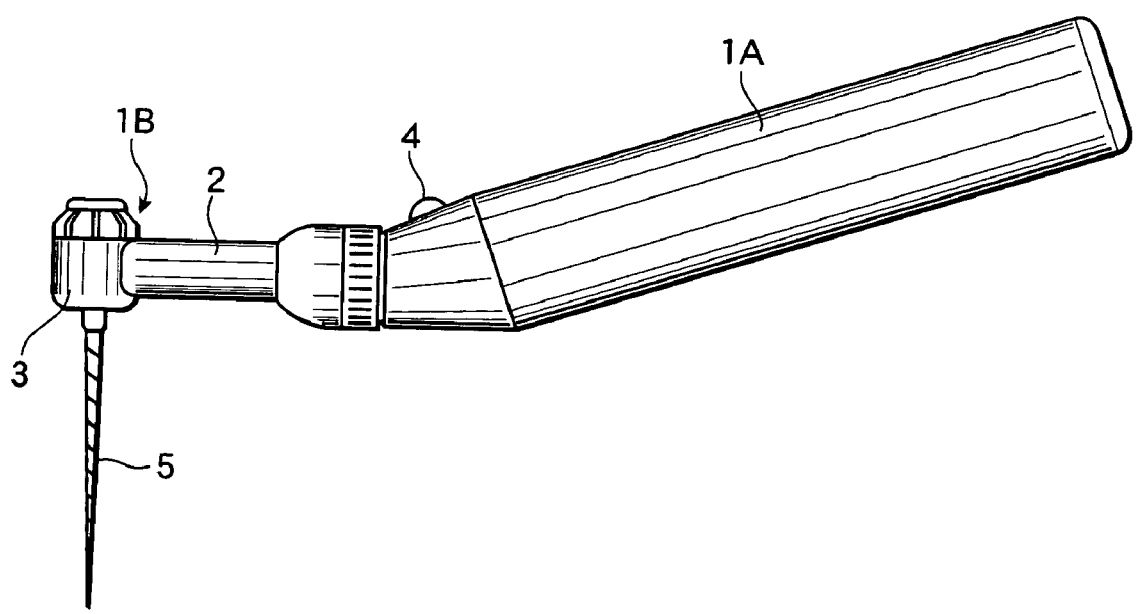
FIG. 4 is a side view of a conventional endodontic handpiece having a head unit.

Referring to FIGS. 1 to 3, dental head unit 10 according to the present invention includes head section 10B having sleeve 19 rotatably supported therein for detachably receiving cutting tool 18, and neck section 10A extending proximally from the head section 10B and having opening 33 in its proximal end for receiving a handpiece body for connection.

The neck section 10A includes shaft 22 having gears 22a, 22b provided on both ends thereof, inner housing 14 rotatably accommodating the shaft 22 by means of distal and proximal bearings 23 and 24, outer housing 13 in which the inner housing 14 is inserted, and rear housing 25 connected onto the proximal end of the outer housing 13. The opening 33 is formed between the rear housing 25 and the inner housing 14.

In the head section 10B, cutting tool 18 is rotatably supported. The cutting tool 18 has grip 18c to be inserted into and held in the sleeve 19 of the head section 10B, and shank 18d extending downwardly from the grip 18c and used for enlarging the root canal in its tip portion. The grip 18c has reduced diameter portion 18b and notch 18a having a D-shaped section in its upper portion.

The head section 10B includes sleeve 19 for detachably holding the grip 18c of the cutting tool 18. The sleeve 19 is rotatably supported in head housing 17 and head collar 26 by means of bearings 20a, 20b. The bearings 20a, 20b not only support the sleeve 19 rotatably, but also vertically position the sleeve 19 in place. On the lower end portion of the sleeve 19, gear 21 is integrally formed for meshing with the gear 22a on the shaft 22. In the upper end portion of the sleeve 19, projection 19a is projected on its inner surface for engagement with the notch 18a of the cutting tool 18. This mutual engagement of the projection 19a and the notch 18a ensures the sleeve 19 to rotate, when driven, with the cutting tool 18, without running idle alone.

In the upper portion of the head housing 17, horizontal slit 17a is formed, into which latch 15 is inserted. The latch 15 has hook 15a in its tip, and is pivotally attached to the head housing 17 with fixture pin 16 threaded in a hole in the head housing 17. The latch 15 is pivoted horizontally around the fixture pin 16 to detachably engage the hook 15a with the reduced diameter portion 18b of the cutting tool 18 for holding the cutting tool 18 in place and preventing it from falling off.

Contact holder 12 in a generally cylindrical form made of a non-conductive material, such as a synthetic resin, is provided on and around the outer housing 13 in an axially slidable manner. The contact holder 12 has urging member 12a such as a spring, and a ball 12b urged by the urging member 12a into engagement in one of slide grooves 13a, 13b, 13c provided in the outer surface of the outer housing 13.

The contact holder 12 further has lead attachment 12d in the form of an aperture, into which contact pin 31 provided at an end of lead 32 is fit for providing electrical contact between contact 11 and a root canal length measuring device (not shown).

Contact 11 made of an electrically conductive material, such as metal, is inserted from its proximal end into the contact holder 12 at a predetermined location, and fixed to the contact holder 12 by pressing annular fixture 11b into the contact holder 12 from the proximal end thereof, and fixing the fixture 11b to the proximal end of the contact 11. Here, the fixture 11b is positioned so as not to be in contact with the outer surface of the outer housing 13. In other words, the contact holder 12 is fixed to the proximal end of the contact 11.

Referring to FIGS. 1 and 2(b), the contact 11 has two rods 11a of a conductive material. The rods 11a extend straight distally from its proximal end, curved downward, and then forward, and in their distal end portions, slightly curved away from each other. The rods 11a are configured generally in a gentle curve so as to disengageably hold the cutting tool 18 between the rods 11a. That is, when shank 18d of the cutting tool 18 is held between the distal end portions of the rods 11a, the rods 11a are in close contact with the shank 18d from both sides, and when the shank 18d is not held between the rods 11a, the rods 11a are in close contact with each other.

The proximal end portions of the rods 11a are arranged on opposite sides of the lead attachment 12d formed in the contact holder 12. When the contact pin 31 is fit in the lead attachment 12d, the contact pin 31 is pressed between the two rods 11a to be in close contact therewith to provide electrical connection between the contact 11 and the contact pin 31, and thus the lead 32.

By sliding the contact holder 12 forward or rearward with respect to the neck section 10A, the contact 11 is brought into or released from contact with the cutting tool 18 for providing or breaking electrical connection between the tool 18 and the contact 11.

The contact holder assembly of the present invention includes the contact holder 12 and the contact 11 discussed above.

The root canal length measuring device to be electrically connected to the contact 11 via the lead 32 is not shown in the drawings, but may be a conventional device. For example, the device may have a body with a meter for indicating the change in the resistance, and two leads extending from the body and each having a connector at its free end. One of the connectors is connected with respect to the root canal forming tool or the probe, in this case the contact pin 31 as the connector is connected to the cutting tool 18 via the contact 11, and the other connector is connected to a metal part such as a saliva ejector. The device is set to indicate a predetermined range of resistance when the tip of the root canal forming tool reaches the apex foramen.

Next, operation of the dental head unit 10 according to the present invention will be explained.

Referring to FIG. 3, for detaching the cutting tool 18 from the dental head unit 10, the latch 15 is pivoted around the fixture pin 16 to disengage the hook 15a from the reduced diameter portion 18b of the cutting tool 18. This allows the grip 18c of the cutting tool 18 to be disengaged and removed from the sleeve 19.

The contact 11 in the state shown in FIGS. 1 and 2(b) may be disengaged from the shank 18d of the cutting tool 18 into the state shown in FIG. 3, simply by sliding the contact holder 12 proximally with respect to the outer housing 13, which causes the contact 11 also to slide proximally to be disengaged from the shank 18d. Here, the ball 12b in the contact holder 12, which has been fit in the distal slide groove 13a under the urging force of the urging means 12a, moves out of the groove 12a as the contact holder 12 is slid against the force of the urging means 12a, rolls along the slide groove 13b into the proximal slide groove 13c, and fits in the latter. In this way, the urging means 12a, the ball 12b, and the slide grooves 13a, 13b, 13c, cooperate to limit the axial movement of the contact holder 12 within a predetermined range, and ensure to hold the contact holder 12 in the positions as shown in FIGS. 1 and 3 when the contact holder 12 is not drawn to move in the axial direction.

It is preferred to remove the contact pin 31 from the lead attachment 12d before axially sliding the contact holder 12, but the contact holder 12 may be slid with the contact pin 31 fitting in the lead attachment 12d.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental head unit capable or measuring a root canal length of a patient, comprising:
    a head section having a sleeve rotatably supported therein for detachably holding a cutting tool therein;
    a neck section extending proximally from said head section and having a proximal end for connecting to a handpiece body;
    a contact capable of detachably contacting the cutting tool for providing electric connection to the cutting tool when in contact; and
    a contact holder fixed to a proximal end of said contact;
    wherein said contact holder is axially slidable with respect to said neck section, said contact holder has a lead attachment to which a lead for electrically connecting said contact to a root canal length measuring device is detachably attached, and said contact holder is provided on and around said neck section.

2. The dental head unit of claim 1, wherein said contact comprises two rods, each having a distal end portion configured to disengageably hold said cutting tool between said two rods.

3. The dental head unit of claim 2, wherein said two rods are arranged on opposite sides of said lead attachment.

4. The dental head unit of claim 1, wherein said lead attachment is a hole provided in the contact holder.

5. A contact holder assembly for use with a dental head unit of claim 1 having a head section and a neck section, comprising:
    a contact capable of detachably contacting a cutting tool held in a head section of a dental head unit for providing electric connection to the cutting tool when in contact; and
    a contact holder fixed to a proximal end of said contact,
    wherein said contact holder is axially slidable with respect to a neck section of the dental head unit, said contact holder has a lead attachment to which a lead for electrically connecting said contact to a root canal length measuring device is detachably attached, and said contact holder is to be provided on and around said neck section.

* * * * *